United States Patent [19]

Durrwachter et al.

[11] Patent Number: 5,254,753
[45] Date of Patent: Oct. 19, 1993

[54] PRODUCTION OF ARYL ETHANOLS

[75] Inventors: J. R. Durrwachter; G. N. Mott; H. Ramos, Jr.; Ahmed Tafesh, all of Corpus Christi, Tex.

[73] Assignee: Hoechst Celanese Corporation, Somerville, N.J.

[21] Appl. No.: 841,138

[22] Filed: Feb. 25, 1992

[51] Int. Cl.$^5$ .......................................... C07C 29/141
[52] U.S. Cl. ...................................... 568/814; 568/715
[58] Field of Search ........................ 568/715, 814, 811

[56] References Cited

U.S. PATENT DOCUMENTS 4,877,909 10/1989 Mizusaki et al. ................. 568/814
5,003,115 3/1991 Strutz ................................ 568/715

FOREIGN PATENT DOCUMENTS 98881002 4/1976 Canada .............................. 568/814

Primary Examiner—Werren B. Lone
Attorney, Agent, or Firm—James J. Mullen; Donald R. Cassady; Michael W. Ferrell

[57] ABSTRACT

The invention provides a process for preparing aryl ethanols from aryl methyl ketones. The process involves a novel oxidation of the ketone to a dialkylacetal derivative of an aryl glyoxal, which is then hydrolyzed to an aryl glyoxal. The aryl glyoxal is then catalytically hydrogenated to reduce both carbonyl groups simultaneously to yield the aryl ethanol. The process is illustrated by conversion of 4-hydroxyacetophenone to 4-hydroxyphenyl alcohol:

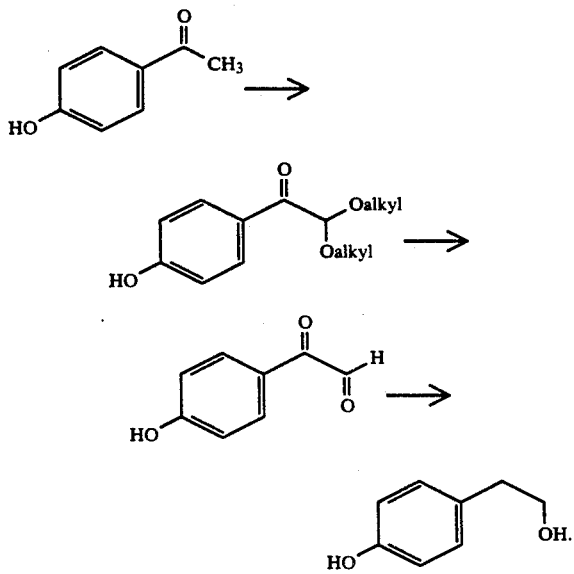

23 Claims, No Drawings

PRODUCTION OF ARYL ETHANOLS

The present invention relates to an improved process for the production of aryl ethanols.

BACKGROUND OF THE INVENTION

Aryl ethanols are important intermediates in the manufacture of chemicals and pharmaceuticals. For example, 4-Hydroxyphenethyl alcohol (4-HPE) is useful as an intermediate in the preparation of several pharmaceutical compounds. U.S. Pat. No. 4,760,182 describes the use of 4-HPE to prepare phenoxypropanolamines, in particular the beta-adrenergic blocking agent, betaxolol. EP patent application No. 249,245 describes the use of 4-HPE for preparing the anti-hypertensiveagents,phenyl (dialkyl)dihydropyridine dicarboxylates. JP 86-201940 describes its use in preparing (aminopropoxyphenyl)alkanols and esters which are employed in the treatment of glaucoma.

Synthesis of 4-HPE has been documented in the past. Yamada et al. *Chem. Pharm. Bill.*, (Tokyo), Vol. 11, pp. 258-260 (1963) describe its preparation from the corresponding amine, which, however, is not readily accessible. Khafagy et al. *J. Med. Chem.*, Vol. 9(6), page 936 (1966) describe its synthesis from 4-hydroxyphenylacetic acid. Hussein, *Angew. Botan.*, Vol. 38(1),pp. 1-43 (1964) reports its synthesis from phenethyl alcohol.

U.S. Pat. No. 5,003,115 (assigned to Hoechst Celanese Corporation) describes the production of 4-HPE from 4-acetoxystyrene.

There is a continuing interest in identifying improved and cost effective methods to prepare aryl ethanols such as 4-HPE, preferably from readily available materials or from materials that may be produced by simple and economical processes.

It has now been found that aryl ethanols can be prepared in high yields and in high purity from aryl methyl ketones, many of which are commercially available. The inventive process involves the oxidative conversion of aryl methyl ketones to ketoacetal derivatives, which can be hydrolyzed to glyoxals, which can then be reduced to aryl ethanols.

SUMMARY OF THE INVENTION

The present invention includes a method for producing aryl ethanols from aryl methyl ketones which comprises (a) oxidizing the aryl methyl ketone using an alkyl nitrite in a mixture of an acid and a primary or secondary alcohol to a dialkylacetal derivative;

(b) hydrolyzing the above dialkylacetal derivative to the corresponding glyoxal; and (c) reducing both carbonyl functionalities of the glyoxal simultaneously to the aryl ethanol.

The present invention further provides a process wherein an arylglyoxal is directly converted to an aryl ethanol by simultaneously reducing both carbonyl groups in the glyoxal compound by catalytic hydrogenation. Combined with the above-described hydrolysis of the acetal derivative to glyoxal, this invention thus provides a surprisingly simple and efficient route to prepare aryl ethanols.

DESCRIPTION OF THE INVENTION

In one embodiment, the present invention provides a process to produce aryl ethanols from aryl methyl ketones. A preferred embodiment of the process is illustrated by a method shown in Scheme 1 to produce 4-HPE from 4-hydroxyacetophenone (4-HAP).

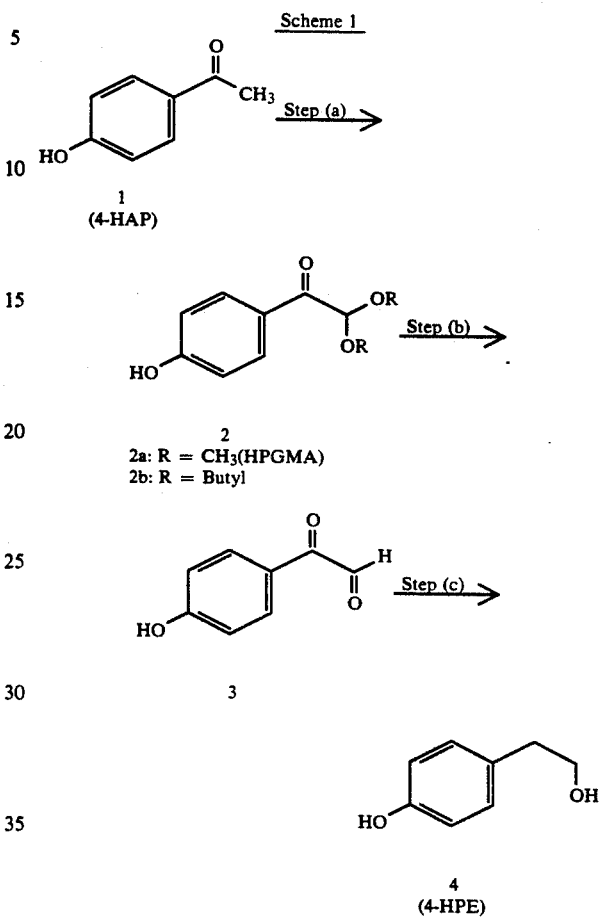

In Scheme 1. step (a) shows the oxidative conversion of 4-HAP (Formula 1) directly and smoothly to the α-ketodialkyl acetal of Formula 2. Conversion of aryl ketones to α-ketodialkylacetals is known before. For example, D. Manning et al describe such a conversion in *Journal of Organic Chemistry*, Vol. 26, page 3755 (1961). The reaction of step (a) is accomplished by oxidizing 4-HAP in a mixture of an acid and a primary or secondary alcohol. Suitable alkyl nitrites include methyl nitrite, isopropyl nitrite, n-butyl nitrite, amyl nitrite, and the like. Suitable acids include hydrochloric, sulfuric, acetic, and the like. The alcohol, as mentioned above, is a primary or secondary alcohol. The nature of the alcohol determines the nature of the alkyl groups in 2. Thus, if methanol is used in step (a), the dimethylacetal 2a (HPGMA) is obtained. On the other hand, if butanol is used, the dibutylacetal 2b is formed. The reaction of step (a) may be performed generally at about −30° C. to 35° C., typically at about −30° C. to about 20° C., and preferably at about 0° C. to about 10° C.

Step (b) describes the hydrolysis of the dialkylacetal of Formula to 4-hydroxyphenylglyoxal (Formula 3). Generally, hydrolysis in an acid medium accomplishes this deprotection reaction. Water may be added, if needed. Suitable acids include, but are not limited to, acetic, hydrochloric, sulfuric, methanesulfonic, acidic ion exchange resins, and the like, and combinations thereof. In a typical example, an acid such as, for example, aqueous acetic acid is added to the compound of Formula 2. and the reaction mixture is refluxed under light vacuum to hydrolyze the acetal and distil off the hydrolysis products, such as the alcohol and acetate ester of the alcohol, to yield the glyoxal of Formula 3. From compound 2a, for example, methanol and methyl acetate are formed and distilled off.

Step (c) involves a simultaneous reduction of both carbonyl groups in the glyoxal compound of Formula 3 to provide 4-HPE (Formula 4). This is accomplished by a catalytic hydrogenation in presence of a transition metal catalyst on an inert support in presence of a solvent. Catalysts such as, for example, Pd, Pt, and mixtures thereof, are useful for this reaction. An example of inert support is carbon. Pd/C and Pt/C are particularly preferred. Generally, polar solvents such as alcohols, acids, ketones, and the like, are useful for this reaction. Some typical solvents include isopropanol, acetic acid, acetone, aqueous sulfuric, aqueous hydrochloric acid, and aqueous methanesulfonic acid solution, and the like. The reduction is generally conducted at about 10°–150° C., typically at about 20°–100° C., and preferably at about 30°–90° C., under about 30–1,000 psi hydrogen pressure generally, and 200–500 psi hydrogen pressure preferably.

More embodiments of the invention arise by possibilities of combining steps in Scheme 1. Thus, by employing steps (a) and (b) successively, 4-HAP may be converted to 4-hydroxyphenylglyoxal efficiently and in high yields. Furthermore, steps (b) and (c) may optionally be combined and run as a one-pot reaction. Such a combination may provide a direct and novel route to produce aryl ethanols from dialkylacetal derivatives of arylglyoxals. Thus, for example, the dibutylacetal of Formula 2b may be taken in a solvent medium such as, for example, a mixture of aqueous hydrochloric and aqueous acetic acid, a catalyst such as Pd/C may be added, and the mixture heated in an autoclave in hydrogen atmosphere at temperatures of about 30°–130° C. for about 5–24 hours, to yield 4-HPE.

The following Examples are provided in order to further illustrate the present invention; however, the invention is in no way limited thereby.

EXAMPLES

In the following Examples, g refers to grams, ml to milliliters, l to liters ° C. to degrees Celsius, rpm to revolutions per minute, psi to pounds per square inch, and ambient temperature to temperatures about 20°–28° C.

Example 1

Preparation of 4-hydroxyphenyl glyoxal dimethylacetal

Two separate reactors were set up: a methyl nitrite generator, and a reaction flask. The methyl nitrite generator consisted of a 2 l round bottom flask equipped with a thermowell, a 500 ml addition funnel, a mechanical stirrer, a nitrogen inlet, and a gas outlet attached to a Tygon TM tubing that led to a fritted gas sparger in the reaction flask. The generator was charged with sodium nitrite (356 g, 5.16 m), methanol (225 ml) and water (225 ml).

The reaction flask was a 3 l three neck round bottom flask equipped with a thermowell, a Friedrich condenser with a gas outlet that led to a vent and the fritted gas sparger from the above generator. The reactor was charged with 4-HAP (272 g, 2 moles) and methanolic HCl (1.25M, 600 ml). The reaction flask was initially chilled to about 0° C. with an isopropanol/dry ice bath. Dilute sulfuric acid (33% aqueous, 568 ml, 6.8 equivalents) was added slowly into the generator to generate methyl nitrite which reacted with the acetophenone in the reaction flask. The temperature of the reaction as maintained at about 0°–5° C. Total addition took about 4 hours. After addition, the reaction mixture was transferred to a 2 l flask with about 500 ml of water. The methanol was removed by rotary evaporation, and cooling of the mixture yielded the desired dimethylacetal which was then filtered and dried. The product was pure enough to be used in further reactions. (Yield: 57%). The structure was confirmed by NMR analysis.

Example 2

Preparation of the diisopropylacetal of 4-hydroxyphenyl glyoxal

This reaction did not need a separate generator for propyl nitrite since it is stable and commercially available. In a similarly set up reaction flask as in Example 1, isopropanol (100 ml), 4-HAP (40 g, 0.294 mole) and isopropyl nitrite (62 ml, 2 equivalents) were charged and stirred to dissolve. The solution was then cooled to 0° C., and acidic isopropanol (100 ml isopropanol containing about ⅛ HCl by volume) was added at such a rate as to maintain a temperature of less than 25° C. More isopropyl nitrite (25 ml) was then added. The reaction was monitored by HPLC. After addition was completed, the reaction was allowed to stand overnight at ambient temperature. Then 400 ml water was added when the oily product separated out. The product was separated by decantation, dissolved in an equal volume of methylene chloride, transferred to a separatory funnel, and was washed with water (2×200 ml) and then brine (2×200 ml). Removing the solvent by rotary evaporation, and recrystallization from methyl tert-butyl ether:hexane (1:1 v/v) gave the pure acetal, whose structure was confirmed by NMR.

Example 3

Preparation of diisoamylacetal of 4-hydroxyphenyl glyoxal

This was prepared following the procedure in Example 2, but with isoamyl nitrite and isoamyl alcohol substituting for isopropyl nitrite and isopropyl alcohol respectively. The product was isolated in 62% yield, and analyzed as in Example 2.

Example 4

Preparation of dibutylacetal of 4-hydroxyphenyl glyoxal

This was prepared by using butyl nitrite and butanol in the reaction of Example 2. Product was isolated and analyzed in a similar manner.

Example 5

Preparation of 4-hydroxyphenyl glyoxal

The dibutylacetal of Example 4 (29.3 g, 0.105 m), acetic acid (150 ml), methanesulfonic acid (5 ml) and water (150 ml) were taken in a round bottom flask fitted with a distillation set up, heated to reflux under vacuum. With pot temperature around 50°–60°, butanol and butyl acetate were distilled off. The mixture was then refluxed at atmospheric pressure for about an hour, when an organic layer separated. This organic layer was isolated by decantation. Liquid chromatography analysis indicated the product to be 4-hydroxyphenyl glyoxal.

Example 6

Preparation of 4-hydroxyphenylglyoxal from 4-HAP

A methyl nitrite generator and a reaction flask were set up as in Example 1. For generation of the gas, NaNo$_2$ (303.6 g, 4.4 moles, 2.2 eq.), water (455.4 g) and methanol (900 ml) were taken in the generator; and dilute hydrochloric acid (450 ml concentrated HCl+80 ml water) were taken in the addition funnel. The reaction flask contained 4-HAP (272.3 g, 2 moles, 1 eq.) and methanolic HCl (1089 ml, 1M HCl in methanol). With the reaction flask cooled to about −5° C., methyl nitrite was generated by adding the HCl into the generator and let in to the reaction at such a rate that the reaction temperature was maintained at about 0°-5° C. The addition lasted about 3 hours, after which the reaction was allowed to warm up to room temperature and then stir overnight. Disappearance of 4-HAP and formation of the dimethylacetal were monitored by liquid chromatography. Upon completion, the reaction mixture was transferred to a 5 liter flask with an equal volume of water. The flask was then fitted with a distillation head, and distilled to remove methanol. When the overhead temperature reached about 100° C., distillation was stopped, and cooled in an ice bath to precipitate the product of Formula 3, which was then filtered and dried. Average yield: 55°-70%.

Example 7

Preparation of 4-HPE from 4-hydroxyphenyl glyoxal

The glyoxal from Example 6 (7 g), Pd/C catalyst (5%, 4 g), and a solution of methanesulfonic acid in water (1M, 150 ml) were charged into a 300 ml autoclave reactor. The reactor was then sealed and purged with nitrogen twice, following which it was charged with hydrogen (200 psi). The reaction mixture was stirred at 1500 rpm for 3 hours, while the temperature was raised from ambient to about 90° C. over this time. Then the reaction was stirred overnight at this temperature. After about 20 hours of total reaction, about 62 psi of hydrogen had been consumed. The reactor was then cooled, vented, and purged with nitrogen. The reaction mixture was removed and filtered through Celite TM. The filtrate was extracted with ethyl acetate (200 ml) in a separatory funnel, and the ethyl acetate layers were washed with saturated NaHCO$_3$ solution (200 ml), and then with water (200 ml). It was then dried over anhydrous MgSO$_4$, filtered and rotary evaporated to yield 4-HPE as a crystalline solid (2 g, 40% yield).

Example 8

Preparation of 4-HPE from 4-hydroxyphenyl glyoxal dimethylacetal in isopropanol solvent The dimethylacetal from Example 1 (20 g) was dissolved in aqueous HCl (1%, 100 ml) in a 250 ml round bottom flask, which was equipped with a distillation head. The mixture was heated to boiling using a heating mantle, when a mixture of methanol and water (about 40 ml) was removed. The remaining slurrious material was then transferred to a 300 ml autoclave reactor along with isopropanol (75 ml). Pd/C catalyst (10%, 4 g) was added, the reactor was sealed and hydrogenation conducted at about 50° C. for about 19.5 hours as in Example 7. A total of 213 psi of hydrogen had been consumed. A similar work-up as in Example 7 yielded 4-HPE as a crystalline solid (7.16 g, 56% yield).

Example 9

Preparation of 4-HPE from 4-hydroxyphenyl glyoxal dimethylacetal in dry acetic acid solvent The dimethylacetal from Example 1 (20 g) was dissolved in glacial acetic acid (400 ml) in a 500 ml reaction flask. The strong acid ion exchange resin, the Dowex 50 TM resin (from Dow Chemical Company, Midland, Michigan) (5 g) was added and the reaction heated to distil off a mixture of acetic acid and methyl acetate. When completion of reaction was indicated by analysis (high pressure liquid chromatography), the reaction was cooled, the ion exchange resin was filtered off, and the filtrates were transferred to an autoclave (300 ml capacity). It was hydrogenated over Pd/C (5%, dry) in hydrogen (200 psi) at room temperature overnight, the temperature was then raised to 120° C. over an 8 hour period and maintained at that temperature for 16 hours. Working up the reaction as in Example 7 yielded the acetate ester of 4-HPE which was hydrolyzed in methanolic HCl to yield 4-HPE (50% yield).

What is claimed is:

1. A method for producing aryl ethanols which comprises
   (a) providing an aryl methyl ketone of the formula

wherein Ar is an unsubstituted or substituted phenyl, or naphthyl radical, wherein the substituents are selected from the group consisting of hydroxyl, alkoxy, alkyl, phenyl, benzyl, sulfonic acid, and sulfonic acid radicals, wherein the alkyl substituent is a branched or unbranched D1-C8 alkyl radical, wherein said alkyl, phenyl, and benzyl radicals are unsubstituted or substituted with one or more substituents selected from hydroxyl, sulfonic acid, and sulficin acid radicals, and wherein siad phenyl and benzyl substituents are unsubstituted or substituted with a C1-C8 alkyl or C1-C8 alkoxy radical or both;
   (b) oxidizing said aryl methyl ketone, using an alkyl nitrite in a mixture of a suitable acid and a primary or secondary alcohol at about −30° C. to about 35° C. to a ialkylacetal derivative of an aryl glyoxal wherein said alcohol contributes the alkyl groups in said dialkylacetal derivative;
   (c) hydrolyzing said dialkylacetal derivative at about 15°-150° C. in an acid medium to its corresponding aryl glyoxal; and
   (d) hydrogenating said aryl glyoxal in the presence of a transition metal catalyst on an inert support in a suitable solvent at about 10°-150° C. and at a hydrogen pressure of about 30–1,000 psi to aryl ethanol.

2. The method as described in claim 1, wherein Ar is 4-hydroxyphenyl.

3. The method as described in claim 1, wherein said primary or secondary alcohol in step (b) is selected from the group consisting of methanol, ethanol, the propanols, the butanols, the pentanols, and the hexanols.

4. The method as described in claim 3, wherein said alcohol is methanol.

5. The method as described in claim 3, wherein said alcohol is n-butanol.

6. The method as described in claim 1, wherein said alkyl nitrite is methyl nitrite.

7. The method as described in claim 1, wherein said alkyl nitrite is tert-butyl nitrite.

8. The method as described in claim 1, wherein said acid in step (b) is selected from the group consisting of hydrochloric, sulfuric, and acetic acids.

9. The method as described in claim 1, wherein said acid in step (b) is hydrochloric acid.

10. The method as described in claim 1, wherein said acid in step (b) is acetic acid.

11. The method as described in claim 1, wherein said acid medium in step (c) comprises acetic acid.

12. The method of claim 11, wherein said acetic acid further contains catalytic amounts of methanesulfonic acid.

13. The method as described in claim 1, wherein said catalyst in step (d) comprises palladium-on-carbon.

14. The method as described in claim 1, wherein said catalyst in step (d) comprises platinum-on-carbon.

15. A method of producing 4-hydroxyphenethyl alcohol from 4-hydroxyacetophenone, which comprises
(a) oxidizing said acetophenone to a dialkylacetal derivative of 4-hydroxyphenyl glyoxal using an alkyl nitrite in a mixture of a suitable acid and a primary or secondary alcohol at about −30° C. to about 35° C., wherein said alcohol contributes the alkyl groups in said dialkylacetal derivative;
(b) hydrolyzing said dialkylacetal derivative in an acid medium at about 15°150° C. to 4-hydroxyphenyl glyoxal; and
(c) hydrogenating said glyoxal in the presence of a transition metal catalyst on an inert support in a suitable solvent at about 10°–150° C. and at a hydrogen pressure of about 30–1,000 psi, whereby both carbonyl groups of said glyoxal are simultaneously reduced to give 4-hydroxyphenethyl alcohol.

16. The method as described in claim 15, wherein said alcohol in step (a) comprises methanol.

17. The method as described in claim 15, wherein said catalyst on inert support in step (c) is palladium-on-carbon.

18. A method of selectively making an aryl ethanol from an arylglyoxal by catalytically hydrogenating said aryl glyoxal in the presence of hydrogen, and in the presence of a transition metal catalyst on an inert support, in a suitable solvent, at about 10°150° C. and at a hydrogen pressure of about 30–1,000 psi, wherein aryl refers to an unsubstituted or substituted phenyl, or naphthyl radicals, wherein the substituents are selected from the group consisting of hydroxyl, alkoxy, alkyl, phenyl, benzyl, sulfonic acid, and sulfinic acid radicals, wherein the alkyl component is a branched or unbranched C1–C8 alkyl radical and wherein said alkyl, phenyl, and benzyl radicals are unsubstituted or substituted with one or more substituents selected from hydroxyl, sulfonic acid, and sulfinic acid radicals, and said phenyl and benzyl substituents are unsubstituted or substituted with a C1–C8 alkyl or C1–C8 alkoxy radical or both.

19. The method of claim 18, wherein said catalyst on inert support is palladium-on-carbon.

20. A method of producing an aryl ethanol form a dialkylacetal derivative of an aryl glyoxal which comprises heating a solution of said ialkylacetal derivative in an aqueous acid in the presence of hydrogen and in the presence of a transition metal catalyst on an inert support at temperatures ranging from about 30° C.–150° C., and at hydrogen pressures of about 30–1,000 psi, for about 1–24 hours, wherein aryl refers to an unsubstituted or substituted phenyl, or naphthyl radical, wherein the substituents are selected from the group consisting of hydroxyl, alkoxy, alkyl, phenyl, benzyl, sulfonic acid, and sulfinic acid radicals, wherein the alkyl component is a branched or unbranched C1–C8 alkyl radical and wherein said alkyl, phenyl, and benzyl radicals are unsubstituted or substituted with one or more substituents selected from hydroxyl, sulfonic acid, and sulfinic acid radicals, and said phenyl and benzyl substituents are unsubstituted or substituted with a C1–C8 alkyl or C1–C8 alkoxy radical or both.

21. The method as described in claim 20, wherein said aqueous acid comprises aqueous acetic acid.

22. A method of selectively producing 4-hydroxyphenethyl alcohol from a dialkylacetal derivative of 4-hydroxyphenyl glyoxal which comprises heating a solution of said dialkylacetal derivative in an aqueous acid in the presence of hydrogen and in the presence of a transition metal catalyst on an inert support at temperatures ranging from about 30°–150° C., and at hydrogen pressures of about 30–1,000 psi, for about 1–24 hours.

23. The method as described in claim 22, wherein said catalyst on inert support comprises palladium-on-carbon.

* * * * *